(12) United States Patent
Plochocka

(10) Patent No.: US 6,211,318 B1
(45) Date of Patent: *Apr. 3, 2001

(54) SOLVENT-FREE, FINE WHITE POWDERS OF A COPOLYMER OF MALEIC ANHYDRIDE AND A $C_1$-$C_4$ ALKYL VINYL ETHER SUBSTANTIALLY FREE OF POLY (ALKYL VINYL ETHER, HOMOPOLYMER

(75) Inventor: Krystyna Plochocka, Scotch Plains, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/270,176

(22) Filed: Mar. 16, 1999

Related U.S. Application Data

(63) Continuation-in-part of application No. 08/942,830, filed on Oct. 2, 1997, now Pat. No. 5,939,506.

(51) Int. Cl.[7] .............................. C08K 3/30; C08F 22/04; C08F 6/00
(52) U.S. Cl. ................ 526/271; 526/209; 526/318.2; 524/418; 524/419; 528/497
(58) Field of Search ................................. 526/209, 271, 526/318.2

(56) References Cited

U.S. PATENT DOCUMENTS

| | | | |
|---|---|---|---|
| 2,047,398 | * 7/1936 | Voss et al. . | |
| 2,782,181 | * 2/1957 | Verburg et al. . | |
| 3,003,988 | * 10/1961 | Germann et al. . | |
| 3,868,432 | * 2/1975 | Keegan et al. | 260/874 |
| 4,962,185 | * 10/1990 | Tazi et al. | 528/497 |
| 5,147,963 | * 9/1992 | Plochocka et al. | 526/322 |
| 5,214,089 | * 5/1993 | Login et al. | 524/418 |
| 5,369,145 | * 11/1994 | Gasman et al. | 523/120 |
| 5,449,715 | * 9/1995 | Plochocka et al. | 524/556 |
| 5,939,506 | * 8/1999 | Plochocka | 526/272 |

OTHER PUBLICATIONS

"Polymer Handbook", 2–d edition, J. Brandrup, J. Willey & Sons, NY, pp. 11–391–98, 1974.*

* cited by examiner

Primary Examiner—David W. Wu
Assistant Examiner—Tanya Zalukaeva
(74) Attorney, Agent, or Firm—Walter Katz; William J. Davis; Marilyn J. Maue

(57) ABSTRACT

Solvent-free, fine white powders of a copolymer of maleic anhydride and a $C_1$–$C_4$ alkyl vinyl ether substantially free of poly(alkyl vinyl ether) homopolymer.

9 Claims, No Drawings

SOLVENT-FREE, FINE WHITE POWDERS OF A COPOLYMER OF MALEIC ANHYDRIDE AND A $C_1$-$C_4$ ALKYL VINYL ETHER SUBSTANTIALLY FREE OF POLY (ALKYL VINYL ETHER, HOMOPOLYMER

CROSS-REFERENCE TO RELATED PATENT APPLICATIONS

A solvent-free process for making copolymers of maleic anhydride and an alkyl vinyl ether is described in continuation-in-part U.S. patent application Ser. No. 08/942,830, filed Oct. 2, 1997, now U.S. Pat. No. 5,939,506.

BACKGROUND OF THE INVENTION

1. Field of the Invention

This invention relates to copolymers of maleic anhydride and a $C_1$–$C_4$ alkyl vinyl ether, and, more particularly, to copolymers which are substantially free of poly(alkyl vinyl ether) homopolymers therein.

2. Description of the Prior Art

Copolymers of maleic anhydride (MAN) and a $C_1$–$C_4$ alkyl vinyl ether (AVE) have been described extensively in the art. However, such copolymer products invariably include homopolymers of poly(alkyl vinyl ether) as an impurity as a result of homopolymerization of excess alkyl vinyl ether present in the reaction mixture. The presence of this poly(alkyl vinyl ether) impurity adversely affects the performance of any hydrolyzed copolymer product made therefrom, in personal and oral care compositions. Particularly, this impurity imparts objectionable color and haze to such compositions.

Accordingly, it is an object of the present invention to provide solvent-free, fine white powders of a copolymer of maleic anhydride and a $C_1$–$C_4$ alkyl vinyl ether free of poly(alkyl vinyl ether) homopolymer to the extent of the detection limit of NMR analysis, which is <1 molar % of the homopolymer.

Another object of the invention is to provide a solvent-free process for making such high purity copolymers.

A feature of the invention is the inclusion of a suppressor agent in the reaction mixture of maleic anhydride and excess alkyl vinyl ether and radical initiator. The suppressor agent is present therein in an amount sufficient to prevent cationic homopolymerization of alkyl vinyl ether monomer during the radical copolymerization of these monomers.

Another feature of the invention is to provide hydrolyzed copolymers of maleic anhydride and alkyl vinyl ether free of homopolymers of alkyl vinyl ether which are without color or haze.

SUMMARY OF THE INVENTION

What is described herein are solvent-free, fine white powders of a copolymer of maleic anhydride and a $C_1$–$C_4$ alkyl vinyl ether which is substantially free of poly(alkyl vinyl ether) homopolymer.

A feature of the invention is the provision of the copolymer which is free of said homopolymer to the extent of the detection limit of NMR analysis.

Preferably the suppressor agent is present in an amount of about 500 to 5000 ppm by weight of the alkyl vinyl ether monomer used in the process.

Suitable suppressor agents to preclude cationic homopolymerization of alkyl vinyl ether include water, alcohols, ammonia, amines, hydroxyamines, amides or carboxylic acids, trialkyl- or triaryl- phosphines, thiophenes and esters. Water is preferred.

DETAILED DESCRIPTION OF THE INVENTION

In accordance with the invention, there is provided a solvent-free process for making solvent-free, fine white powders of copolymers of maleic anhydride and a $C_1$–$C_4$ alkyl vinyl ether, preferably methyl vinyl ether, MVE, which are substantially free of homopolymers of alkyl vinyl ether monomer, i.e. poly(alkyl vinyl ether) homopolymers. These homopolymers ordinarily are produced by homopolymerization of excess alkyl vinyl ether present in the reaction mixture.

In this invention, an alkyl vinyl ether homopolymerization suppressor agent is included in the reaction mixture which thwarts cationic homopolymerization of the alkyl vinyl ether monomer while the desired free radical copolymerization of maleic anhydride and alkyl vinyl ether monomers can occur readily.

Suitable suppressor agents for use herein include water, alcohols, ammonia, amines, hydroxyamines, amides, phosphines, thiophene, carboxylic acids and esters. Water is most preferred.

Preferably water as the suppressor agent is present in a sufficient amount of about 500 to 5000 ppm by weight of the alkyl vinyl ether. Of course, an amount in excess of sufficient may be used, if desired.

Suitably the MAN:MVE mole ratio is at least 3, preferably 25:1 to 5:1, and, most preferably 12:1 to 7:1. The % solids level during polymerization is about 10–40%.

The free radical initiator concentration is about 0.01 to 0.2%, preferably 0.05 to 0.1%, by weight, based on the copolymer obtained.

Usually, varying concentrations of homopolymer are found in the copolymer product. The use of suppressor agent during copolymerization reduces this amount to a level under the detection limit for NMR analysis of the copolymer, i.e. <1 molar % of homopolymer.

After polymerization is complete, the excess MVE is stripped off and the copolymer is dried at about 40–100° C. under vacuum.

The invention will now be described with reference to the following examples, in which:

EXAMPLE 1

A 1-liter Buchi pressure reactor was sparged with nitrogen and charged with 300 g of methyl vinyl ether MVE (5.16 mol) and 0.055 g of Trigonox® 21 (t-butylperoxy-2-ethylhexanoate, Akzo Nobel Chemicals Inc.), (a concentration of 0.08% based on the copolymer obtained), rinsed in with MVE. Then 3000 ppm of water was added (based on MVE). The precharged reactor was heated to 75° C. with agitation over a period of 15 min. Then 41 g (0.418 mol) of molten maleic anhydride MAN (MVE:MAN of 15:1) was fed in over a period of 1 hr. The solids content of the resultant reaction mixture was 16%. The temperature was maintained at 75° C. for 1.5 hours. Then excess MVE was stripped off whereupon the pressure dropped to atmospheric. Upon opening the reactor, a fine, free-flowing copolymer powder product was observed. The product obtained was dried in a vacuum oven at 65° C. for 4 hours to remove any traces of remaining MVE.

A total of 64.8 g of a fine, free-flowing powder was recovered (99.37% of theoretical yield). The product was a 1:1 MAN:MVE copolymer (based on $^{13}$C NMR), having a specific viscosity of 3.6 (1% w/v in methyl vinyl ketone at 25° C.). Less than 1% poly(methyl vinyl ether) homopolymer was detected by such NMR analysis.

The haze and APHA color of a 13% aqueous solution of the copolymer were correspondingly only 25 NTU/60, indicating a substantially haze and color-free hydrolysis product of the copolymer had been obtained. The flavor characteristic in an oral care composition was completely acceptable.

EXAMPLE 2

The procedure of Example 1 was followed using 5000 ppm of water added to the precharged reaction mixture. Poly(methyl vinyl ether) homopolymer was undetectable by NMR analysis. The specific viscosity of the copolymer was 3.0. The haze and APHA color of a 13% aqueous solution was 20/45, respectively, and the flavor in an oral care composition was completely acceptable.

While the invention has been described with particular reference to certain embodiments thereof, it will be understood that changes and modifications may be made which are within the skill of the art. Accordingly, it is intended to be bound only by the following claims, in which:

What is claimed is:

1. Solvent-free, fine white powders of a copolymer of maleic anhydride and a $C_1$–$C_4$ alkyl vinyl ether substantially free of poly(alkylvinyl ether) homopolymer.

2. The copolymer of claim 1 which is free of said homopolymer to <1 molar %, as determined by NMR analysis.

3. A solvent-free process for making fine white powders of a copolymer of maleic anhydride and an alkyl vinyl ether substantially free of poly(alkyl vinyl ether), by copolymerization of maleic anhydride (MAN) and excess alkyl vinyl ether (AVE) monomers and a free radical initiator to promote radical copolymerization of said monomers, which comprises including in the reaction mixture an effective amount of water as a suppressor agent sufficient to preclude cationic homopolymerization of alkyl vinyl ether monomer into poly(alkyl vinyl ether) homopolymer, said amount being about 500 to about 5000 ppm.

4. A solvent-free process according to claim 3 wherein the free radical initiator is present in an amount of 0.01 to 0.2% by weight based on copolymer obtained.

5. A solvent-free process according to claim 3 which is run at 10–40% solids.

6. A solvent-free process according to claim 3 wherein the alkyl vinyl ether:maleic anhydride mole ratio is at least 3.

7. A solvent-free process according to claim 6 in which said ratio is about about 25 to about 6.

8. A solvent-free process according to claim 3 in which molten maleic anhydride is fed into the precharged reaction mixture of excess alkyl vinyl ether, free radical initiator and suppressor agent during a predetermined period of time.

9. A solvent-free process according to claim 3 in which the polymerization product is dried under vacuum at 40 to 100° C. to remove any traces of alkyl vinyl ether and any remaining suppressor agent.

\* \* \* \* \*